United States Patent [19]

Golde et al.

[11] 4,438,032

[45] Mar. 20, 1984

[54] UNIQUE T-LYMPHOCYTE LINE AND PRODUCTS DERIVED THEREFROM

[75] Inventors: David W. Golde; Shirley G. Quan, both of Los Angeles, Calif.

[73] Assignee: The Regents of the University of California, Berkeley, Calif.

[21] Appl. No.: 456,177

[22] Filed: Jan. 6, 1983

Related U.S. Application Data

[63] Continuation of Ser. No. 229,900, Jan. 30, 1981, abandoned.

[51] Int. Cl.$^3$ .................. C12P 21/00; C12N 15/00; C12R 1/91; C07G 7/00
[52] U.S. Cl. ...................... 260/112 R; 260/112 B; 424/85; 424/177; 435/68; 435/172; 435/240; 435/241; 435/948
[58] Field of Search .................. 260/112 R, 112 B; 435/68, 172, 240, 241, 948

[56] References Cited

U.S. PATENT DOCUMENTS 4,338,397  7/1982  Gilbert .................................. 435/68

OTHER PUBLICATIONS

Saxon et al., Annals of Internal Medicine, (1978), 58:323–326.
Weisbart et al., Clin. Immunology & Immunopathology, (1979), 14:441–448.
Weisbart et al., J. Lab. Clin. Med., (1979), 93:622–626.
Lusis et al., In Viva and In Vitro Erythropoiesis, 1980, pp. 97–106.
Golde et al., Blood, (1978), 51:1068–1071.
Golde et al., PNAS, USA, (1980), 77:593–596.
Golde et al., Annals of Internal Medicine, (1980), 92:650–662.

*Primary Examiner*—Howard E. Schain
*Attorney, Agent, or Firm*—Bertram I. Rowland

[57] ABSTRACT

Human T-lymphoblast cell line, Proteinaceous products produced therefrom, messenger RNA and DNA expressing the proteinaceous products. A human T-lymphoblast cell line (Mo) maintained as a continuous culture constitutively produces proteins, including immune interferon, neutrophil migration inhibition factor, granulocyte-macrophage colony-stimulating activity and erythroid-potentiating activity, as well as other proteins produced by T-cells.

22 Claims, No Drawings

UNIQUE T-LYMPHOCYTE LINE AND PRODUCTS DERIVED THEREFROM

The invention described herein was made in the course of or under a grant from the United States Public Health Service.

CROSS-REFERENCE TO RELATED APPLICATIONS

This application is a continuation of pending prior application Ser. No. 229,900, filed Jan. 30, 1981. Now abandoned.

Field of the Invention

Cell regulation is mediated by a wide variety of polypeptides. Historically, few of these polypeptides are produced in sufficient amount to be isolated and characterized. Even in those situations where a particular polypeptide was capable of isolation and characterization, the number of amino acids constituting the polypeptide normally precluded synthesis by conventional peptide bond formation in commercially useful amounts.

In the last few years a number of discoveries have occurred which at the present time promise opportunities for the detection, isolation, and production in commercially useful amounts of naturally occurring proteins, which fulfill a wide variety of cell regulatory functions.

The ability to insert a gene into a replicating vector, such as a plasmid or phage, and transform a microorganism with the resulting hybrid has introduced new techniques for the production of macromolecular polypeptides. These techniques not only afford the opportunity to obtain polypeptides in abundance, but allow for study of the polypeptides and use of the polypeptides in regulating cell functions in vitro and in vivo.

At the present time, in order to be able to produce a polypeptide of interest by "genetic engineering," there are basically three methods which may be employed. Once the amino acid sequence or DNA sequence is known, for relatively small polypeptides, the sequence can be synthesized. See for example, Wu, R. (1978) Ann. Rev. of Biochem. 47, 607. Alternatively, one can excise the gene either directly, where the chromosome has been mapped and there are available restriction sites adjacent the gene, or indirectly by genomic cloning. Thirdly, one can isolate the messenger RNA and employing reverse transcriptase produce cDNA from which dsDNA may be obtained.

Because of the cumbersome nature and difficulties associated with synthesis and the existence of introns present in chromosomal DNA, the messenger RNA is frequently the desired route where genetic engineering is involved.

In each cell, there is continuously produced a large number of different messenger RNA molecules. Therefore, means must be provided for isolating the messenger RNA of interest from the other messenger RNA molecules. Where a messenger RNA of interest is normally produced in only small amounts as compared to the total amount of messenger RNA, it is frequently desirable, if not necessary, to obtain cells which enhance the amount of messenger RNA of interest present in the cell.

As an alternative to genetic engineering, the ability to culture tumor cells in vitro offers an opportunity for the production of a wide variety of polypeptides. Where the tumor cells do not regulate the production of one or more polypeptides of interest, the tumor cells will constitutively produce these polypeptides. By isolating specific tumor cells and establishing a culture, which can be expanded and maintained for long periods of time, one can directly produce the polypeptides of interest from a "normal" host cell. In this manner, one avoids the need to isolate the gene of interest and perform the numerous steps involved with successful genetic engineering. In addition, where modification of the polypeptide naturally occurs, such as glycosylation, and the modification affects the activity of the polypeptide, it will be observable to employ the native host as the polypeptide source.

Brief Description of the Prior Art

The existence of the Mo line was first described in a series of articles by Golde et al., *Blood* 52:1068–1072, 1978; Saxon et al. *Ann. Intrn. Med.* 88:323–326, 1978 and Saxon et al., *J. Immunol.* 120:778–782, 1978. At no time has the Mo cell line been available to other than the investigators involved with its initial discovery and only the conditioned medium from the cell line has been made available to a limited number of investigators for collaborative work with the original discoverers of the Mo cell line. The following additional articles have been published concerning the Mo cell line: Cline and Golde, *Nature* 277:177–181, 1979; Minden et al., *Blood* 54:186–195, 1979; Weisbart et al. *J. Lab. Clin. Med.* 93:622–626, 1979; Weisbart et al. *Clin. Immunol. Immunopathol.* 14:441–448, 1979; Golde et al. *Proc. Natl. Acad. Sci.* USA 77:593–596, 1980; In, Biochemical Characterization of Lymphokines, edited by A. L. de Weck. Academic Press, New York, 1980 pages 221–225; Lusis and Golde, In In Vivo and In Vitro Erythropoiesis: The Friend System, edited by G. B. Rossi. Elsevier/North-Holland Biomedical Press, Amsterdam, 1980, pages 97–106; and Quan et al., *J. Histochem. Cytochem.* 28:434–440, 1980.

SUMMARY OF THE INVENTION

A cell line (Mo) has been established with spleen cells from a patient with a T-cell variant of hairy-cell leukemia. The cells have been shown to be capable of continuous culture for an indefinite period of time, while maintaining the properties of T-lymphoblasts. The cells constitutively produce a wide variety of proteins, including growth factors, such as colony stimulating factor, useful for the growth of granulocyte-macrophage colonies in vitro and erythroid-potentiating activity, which is capable of potentiating the formation of both large and small human erythroid colonies in vitro; human immune interferon, neutrophil migration-inhibition activity, as well as other polypeptides produced by T-lymphoblast cells many of which are secreted and isolatable from the medium.

The cells provide a continuous source of the above proteins, as naturally modified which can be isolated by conventional ways. In addition, due to the constitutive production of the proteins, the cells provide either directly or indirectly, a source of the genes for the proteins of interest, which by conventional genetic engineering techniques, can be introduced into microorganisms for continuous large scale production of the proteins.

DESCRIPTION OF THE SPECIFIC EMBODIMENTS

A novel cell line was established, referred to as the Mo cell line. The cell line was established with spleen cells from a patient with a T-cell variant of hairy-cell leukemia. The cells have been shown to be capable of growing in continuous culture for an indefinite period while maintaining the properties of T-lymphoblasts. More than 60% of the cells rosette with sheep erythrocytes and carry the tartrate-resistant isozyme five of acid phosphatase, characteristic of hairy-cell leukemia. No evidence of immunoglobulin synthesis was observed. The Mo cells are not infected with Epstein-Barr virus and are lysed by antithymocyte globulin in the presence of complement. The cells respond to the mitogen phytohemagglutinin by increased incorporation of [$^3$H] thymidine.

The Mo cell line is conveniently cultured in alpha medium containing 20% fetal calf serum and $10^{-4}$ M α-thioglycerol. While the cell line can also be cultured in serum-free medium, it grows considerably more slowly.

The Mo cell line is unique in liberating many of the products known to be elaborated by lectin- or antigen-stimulated normal T cells. The Mo cell line constitutively produces a wide variety of proteins having different physiological activity in isolatable amounts. Thus, the Mo cell line provides a method for production of a large number of polypeptides of physiologic interest. In addition, because of the constitutive production of these polypeptides, the Mo cell line also offers the messenger RNAs for these polypeptides in relatively large amounts compared to the total amount of messenger RNA present. By employing conventional techniques, the messenger RNAs for the desired polypeptides may be separated from the mass of messenger RNA and used for production of cDNA.

In describing the various products produced by the Mo cell line, the direct production of the polypeptides by the Mo cell line and the isolation of the polypeptides will first be described. This will then be followed by a description of the production of the polypeptides employing hybrid DNA techniques. EPA The first polypeptide of interest is referred to as erythroid-potentiating activity (EPA). This polypeptide enhances the proliferation of human erythroid progenitors in vitro. The polypeptide is an acidic glycoprotein of molecular weight about 45 kdal. The EPA activity in Mo-conditioned medium is bound by DEAE-Sephadex at pH 7.4 and by use of a linear NaCl gradient is eluted from the resin as a single broad peak between 0.15 and 0.25 M NaCl. When subjected to preparative isoelectric focusing in granulated gel, the bulk of the EPA is found in the very acid portions of the gel corresponding to pI 3.5–4.8. The EPA is bound by concanavalin A-Sepharose and most of the activity can be recovered from the lectin by elution with 0.2 M methyl-α-D-mannoside. The EPA is heat stable as evidenced by its retaining substantially all of its activity after heating a Mo-conditioned medium in a boiling water bath for 10 min.

By conventional techniques the EPA can be concentrated and substantially freed of other protienaceous components of the Mo-conditioned medium. Concentrates having a specific activity of at least 25,000 units/mg protein, usually at least 50,000 units/mg protein, are readily obtained by gel exclusion chromatography usually preceded by other techniques e.g. chromatography and electrophoresis. (The unit activity will be defined in the experimental section.)

The EPA in the presence of 0.5 units/ml erythropoietin is active at a concentration less than 0.1 nM, usually less than about 0.01 nM. Stimulation is obtained with both early (14 day BFU-E) and late (7-day CFU-E) human erythroid progenitors.

The subject EPA is important in early events in erythropoiesis. The EPA potentiates the formation of both large and small human erythroid colonies in vitro.

The EPA can find use in enhancing the development of erythrocytes in blood. Other uses for EPA are the production of erythrocytes in vitro, use of EPA in evaluating the ability of stem cells to form erythrocytes, treatment of human host having a deficiency of EPA, and the like.

CSF

The next polypeptide of interest is colony stimulating factor (CSF) which provides in vitro proliferation and differentiation of granulocyte-macrophage progenitors.

The CSF obtained from the Mo cell line is heat stable, being stable at temperatures up to about 70° C. and about half the activity is recovered after 5 mins. of incubation at 90° C. in 0.02 M sodium phosphate, 0.15 M NaCl, pH 7.2, containing 0.1% bovine serum albumin. The molecular weight is about 34 kdal for the glycosylated polypeptide. The presence of sialic acid is indicated, based on changes in isoelectric focusing after neuraminidase treatment. The removal of sialic acid did not affect the activity of the polypeptide. The pI is between pH 4.0 and 5.2. With ion-exchange chromatography, elution from DEAE-Sephadex (equili-brated with 0.02 M Tris, pH 7.4) is between 0.12 and 0.22 M NaCl from serum-free medium, while between 0.18 M and 0.22 M NaCl from serum-containing conditioned medium. The CSF is not inactivated by mercapto ethanol in concentrations as high as 0.1 M in the absence of denaturants, such as 8 M urea.

By conventional purification techniques, such as combinations of affinity chromatography and gel exclusion chromatography, CSF can be obtained in concentrates having a specific activity of greater than 0.5 units/mg, usually greater than 3.5 units/mg protein and preferably greater than 10 units/mg protein. (Units will be defined in the experimental section.) The CSF from the Mo-cell conditioned medium is more active than leukocyte CSF in stimulating granulocyte-macrophage colonies and relatively inert in stimulating mouse granulocyte-macrophage colonies from bone marrow cells.

The CSF can be used for assaying stem cells for the ability to form granulcytes and macrophage, to grow granulocytes and macrophage in vitro, and to enhance the formation of granulocytes and macrophage in a host which is deficient in CSF.

NIF-T

The next protein of interest is neutrophil migration inhibition factor (NIF-T). The neutrophil migration inhibition factor is a heat stable 35-45 kdal glycoprotein resistant to diisopropyl fluorophosphate and reversibly inhibites neutrophil migration.

Type 2 immune interferon

In addition to the other proteins, immune interferon, Type 2 is observed. The presence of interferon was established by assays employing human fibroblasts and vesicular stomatitis virus in a classical plaque-reduction assay for interferon. The fact that it is immune interferon Type 2 was established by its instability at pH 2; instability upon heating, abolishment of the activity by exposure to an antibody to Type 2 interferon; the absence of augmentation of interferon activity by exposure to usual Type 1 inducers, including poly-IC and Sendai virus; and induction of interferon formation by exposure to phytohemagglutinin.

Other Factors

The Mo-cell line interferon is substantially free of other interferons. The Type 2 interferon may be produced by stimulation with lectins to concentrations of greater than about 4000 units/ml, even greater than about 10,000 units per ml. (For units/ml, see Stewart et al., (1977) Proc. Natl. Acad. Sci. USA 74, 4200–4204.)

Interferon purification can be achieved using control-pore-glass beads with ethylene glycol stepwise elution (Wiranoska-Stewart et al., In, Biochemical Characterization of Lymphokines, supra). Further purification can be achieved by dialysis and applying the residue to a poly-U-Sepharose column with sequential chromatographic purification. Specific activities of at least about $10^6$ units/mg protein are achieved.

In addition to the other indicated protein factors, activity was observed for macrophage-activating factor, a factor that stimulates colony formation by human leukemic cells in vitro and a factor that stimulates megakaryocyte growth in vitro.

The Mo cell line can be used for providing the conditioned medium having all of the above factors. As to each of the factors, the proteins can be separated by electrophoresis, chromatography, including affinity, adsorption, and gel exclusion chromatography, gradient density separations, radial immunodiffusion, ultrafiltration, or other conventional techniques which allow for isolation of a protein based on its structure, charge, molecular weight, shape or combinations thereof.

The conditioned medium prepared from the Mo cell line can be used directly, where one or more of the factors may be destroyed or retained, where such factor does not interfere with the purpose of the conditioned medium. For example, heat labile factors may be removed by heating at 90° C. for 5 min, while retaining heat stable factor activities.

The colony stimulating factor can be concentrated from the Mo medium to a specific activity of at least $3.5 \times 10^6$ colonies per $10^5$ Ficoll-Hypaque-separated human bone marrow cells plated per milligram protein. (Golde and Cline, J. Clin. Invest. 51:2981–2983, 1972). The erythroid-potentiating activity has been concentrated to 51,000 units/mg protein, wherein one unit is the amount required to stimulate human peripheral blood burst forming unit-erythrocyte (BFU-E) by 50% in the presence of 0.5 units/ml human urinary erythropoietin.

The production of the various factors can be used to produce the proteins employing hybrid DNA technology. The individual factors can be isolated as described above and in the experimental portion and a portion of the molecule sequenced to determine the amino acid sequence. A sequence of from 15 to 20 amino acids will usually suffice. Based on the observed sequence, one can translate the amino acid sequence back to an RNA or DNA sequence which would express the particular amino acid sequence. The 45 to 60 base sequence can then be used as a probe to isolate the messenger RNA which is translated to the desired protein. The Mo cells can be lysed and the RNA separated from the DNA. The poly-(A) enriched RNA may then be separated on an oligo dT or -dU column. This will separate the messenger RNA from other RNA which is present.

One can further separate the messenger RNA by electrophoresis and employing the Southern technique, label the probe with $^{32}P$, whereby the probe will hybridize solely to the messenger of interest. Once one has identified the messenger RNA of interest, one can employ preparative electrophoresis and by excising the band identified as having the RNA of interest from the electrophoretic gel, a useful amount of the messenger RNA can be obtained.

Employing common procedures, the gene for the particular protein factor may now be prepared. cDNA may be prepared from the messenger RNA employing reverse transcriptase. The cDNA may then be used as a template for the production of dsDNA which expresses the desired protein. The dsDNA may be further modified by adding control signals such as a promoter, RNA polymerase stop signal, ribosomal start and stop signals or other control signals, as appropriate. These signals can be added by ligation, employing oligomers, by joining the dsDNA to a vector, where the signals are present in the proper reference frame with the dsDNA, by addition of one or more mono- or dinucleotides employing the proper ligase, or other well known conditions.

Conveniently, one can add to the blunt ends of the dsDNA an oligomer having a blunt end and a staggered end, where the staggered end upon binding to a complementary end of a vector provides a restriction site.

The gene as modified may be joined to an appropriate vector for transformation or transfection of bacteria or yeast for replication of the hybrid DNA and expression of the desired gene. The transformant cells are cloned and cultivated under conditions where the desired protein is expressed. When the protein is not excreted, the cells are harvested and lysed in accordance with conventional procedures, and the protein isolated in a conventional manner. Where the protein is excreted, the protein may be extracted from the spent nutrient medium.

The Mo cell line can be employed to produce conditioned media. The Mo cell line can be grown in an appropriate nutrient medium, whereby the growth regulating factors and lymphokines excreted into the medium provide a conditioned medium for the growth of other cells. That is, the conditioned medium can be used for the proliferation and differentiation of stem cells, so as to produce progenitors of erythrocytes and granulocyte-macrophage. As already indicated, the conditioned medium can also be used as a source of the individual proteins serving as the growth factors and lymphokines.

The Mo-cell line is normally grown in a conventional nutrient medium e.g. alpha medium containing fetal calf serum, normally about 20%, and a small amount of a mercaptan, generally about $10^{-4}$ M α-thioglycerol. It can also be grown in a serum-free medium, where the cells grow more slowly.

Case History

A 33-year old white man experienced fatigue, mild abdominal discomfort, and easy bruising during a period of 2 years. On presentation to a physician the patient had massive splenomegaly and mild depatomegaly without associated lymphadenopathy. Although bone marrow could not be aspirated, a bone-marrow biopsy showed diffuse replacement with neoplastic cells typical of hairy-cell leukemia. Hemoglobin count was 8 g/dl, packed cell volume 24%, platelet count 45 000/$\mu$l, leukocyte count 2900/$\mu$l with 26% polymorphonuclear leukocytes. About 20% of the peripheral blood leukocytes showed morphologic characteristics of hairy cells. Serum protein electrophoresis, immunoelectrophoresis, and quantitative serum immunoglobulins were normal. The patient was referred to UCLA Medical Center. Bone-marrow and peripheral blood hairy cells had abundant tartrate-resistant acid phosphatase. In October 1976 the patient underwent splenectomy. The spleen weighed about 6 kg and histopathologic examination showed diffuse infiltration with tartrate-resistant acid-phosphatase-containing hairy cells. Transmission electron microscopy revealed the neoplastic cells to have ultrastructure typical of hairy cells, and several characteristic "ribosome-lamellar complexes" were identified. Liver biopsy showed similar abnormal cells in the portal triads. Post-operatively, absolute platelet and granulocyte counts returned to normal.

EXPERIMENTAL PROCEDURES

Mo cells grow in suspension culture and exhibit the morphology of relatively mature T-lymphoblasts. They are lysed by antithymocyte serum in the presence of complement, do not produce immunoglobulin, and over 60% of the cells rosette with sheep erythrocytes. They contain the tartrate-resistant isozyme 5 of acid phosphatase, a marker for hairy-cell leukemia, and are not infected with Epstein-Barr virus. The line has now been cultured for over three years and 100 passages. It is generally cultured in alpha medium (Flow Laboratories, Inglewood, CA) containing 20% fetal calf serum (screened lot) and $10^{-4}$ M $\alpha$-thioglycerol (Calbiochem, San Diego, CA). It can also be cultured in serum-free medium, where it grows considerably more slowly. The Mo cells are responsive to phytohemagglutinin as judged by increased incorporation of radioactive thymidine and increased production of certain lymphokines, including CSF. The cells do not contain measurable terminal deoxynucleotidyl transferase.

Culture of erythroid progenitors

CFU-E and BFU-E were cultured in methylcellulose (Dow Chemical, Medland, MI) using nomal human bone marrow or peripheral blood, as described in Golde et al. (1977) Science, 196, 1112-1113 and Bersch and Golde, (1978) in In Vitro Aspects of Erythropoiesis, eds. Murphy et al., Springer-Verlag, New York, pp. 252-253. Human bone marrow CFU-E, consisting of clusters of 8 or more hemoglobinized cells, were enumerated after 7-8 days. Human bone marrow and peripheral blood BFU-E, consisting of erythroid colonies of 50 or more cells were counted after 14 days. In contrast to some other investigators the formation of a small number of CFU-E and BFU-E colonies was observed in the absence of added erythropoietin. This apparently results from the presence of low levels of endogenous erythropoietin in fetal calf serum or associated with the target cells. Mouse CFU-E and BFU-E were assayed as described in Bersch and Golde, ibid. The serum-free methylcellulose technique for the culture of erythroid cells was adopted from the procedure of Guilbert and Iscove, (1976) Nature, 263 594-595. The culture medium contained 1% bovine serum albumin (Sigma, St. Louis, MO), transferrin (350 $\mu$g/ml), ferric chloride ($1.6 \times 10^{-6}$ M), sodium selenite ($10^{-7}$ M), insulin (1 ng/ml) and human growth hormone (200 ng/ml). Human urinary erythropoietin was obtained from the Division of Blood Diseases and Resources, National Heart, Lung, and Blood Institute and had an activity of about 44 units/mg protein. Friend erythroleukemia cells (GM-86, clone 745) were cultured in methylcellulose with alpha medium and 0.5% bovine serum albumin. Colonies of 8 or more cells were enumerated after 72 hours.

Culture of granulocyte-macrophage progenitors

Ficoll-Hypaque separated, light density nonadherent cells were prepared from bone marrow and cultured as previously described. Colonies containing 40 or more cells were enumerated after 11-14 days.

Chromatography

Ultrogel AcA 44 was from LKB and concanavalin A-Sepharose and DEAE-Sephadex were from Pharmacia. Concanavalin A-Sepharose chromatography was performed using serum-free Mo-conditioned medium in 0.02 M sodium phosphate, 0.15 M NaCl, pH 7.4, and specifically bound glycoproteins were eluted using 0.2 M methyl-$\alpha$-D-mannoside.

Protease inactivation of EPA

Mo-conditioned medium was incubated in 0.02 M sodium phosphate, 0.15 M NaCl, pH 7.4, with 0.3 mg/ml pronase (Calbiochem) or a buffer control for 1 hour at 37° C. Pronase activity was then destroyed by immersing samples in a boiling water bath for 5 minutes.

Bioassays

Colony stimulating factor (CSF) activity was assayed using a two-layer agar technique. (Golde, D. W. and Cline, M. J., J. Clin. Invest. 51:2981-2983, 1972). The target cells were normally $1 \times 10^5$ Ficoll-Hypaque-separated, light-density bone marrow cells obtained from normal volunteers. Colonies (containing 40 or more cells) were scored after 11 days. One unit of activity is defined as the amount stimulating one colony in $10^5$ separated human bone marrow cells plated. Cellular morphology in the colonies was examined either by staining individual colonies picked from cultures with Wright's stain or by staining entire culture dishes for a lipase activity. (Willcox M. B., et al., J. Histochem. Cytochem. 24:979-983, 1976) The latter method was particularly useful for distinguishing granulocyte and macrophage colonies.

Small erythroid colonies (CFU-E) and large erythroid colonies (BFU-E) were grown in methycellulose using normal human bone marrow and peripheral blood. (Golde, D. W. et al. Proc. Natl. Acad. Sci. USA 77:593-596, 1980).

Comparative Studies Utilizing CSFs from Placental- and Leukocyte-conditioned Medium (CM)

Placental CM was prepared as described in Nicola, N.A. et al., Leukemia Res. 2:313-322, 1978. Using 50 $\mu$l of the resulting CM, about 70 colonies were stimulated with the clonogenic human bone marrow CFU-G,M assay described; approximately the same number of colonies was stimulated by a peripheral leukocyte underlayer. Phytohemagglutinin-stimulated leukocyte-conditioned medium was prepared by culturing Ficoll-Hypaque-separated peripheral blood mono-nuclear cells ($3 \times 10^6$ cells/ml) in alpha medium containing 20% fetal calf serum and phytohemagglutinin (Wellcome Research Laboratories) (Price, G. B. et al., Biochem. J. 148:209-217, 1975). Using 50 $\mu$l of the resulting CM, about 60 colonies were obtained with the clonogenic human bone marrow CFU-G,M assay.

The CSFs from placental CM, phytohemagglutinin-stimulated leukocyte CM, and Mo CM (serum containing) were then partially purified by gel exclusion chromatography to remove any inhibitors of granulocyte-macrophage colony formation. The CM from each source was first concentrated about five-fold by ultrafiltration (Amicon apparatus equipped with a PM10 membrane) and then chromatographed on an Ultrogel AcA 44 column equilibrated with 0.02 M sodium phosphate, 0.15 M NaCl, pH 7.4. The major peak of CSF activity from each source eluted in a volume corresponding to molecular weight between 30,000 and 40,000. The fractions containing the bulk of the activity were pooled and utilized for comparative studies of CSFs from these sources. The degree of purification of CSF from each source was about 20-fold.

Purification of Mo CSF

Serum-free Mo CM (1.8 liter) was concentrated by ultra-filtration (using an Amicon apparatus equipped with a PM10 membrane) to 8 ml. The solution was then heated at 57° C. for 30 min and the resulting precipitate removed by centrifugation (9,000 RPM, 15 min, using a Sorvall HB-4 rotor). The clear supernatant solution was applied to a 1.6×78-cm column of Ultrogel AcA 44 (LKB) equilibrated with 0.02 M sodium phosphate, 0.15 M NaCl, pH 7.4, containing 0.01% polyethylene glycol (average molecular weight 6,000). Fractions of 3.8 ml were collected at a rate of 7.2 ml/hr and assayed for CSF activity. The major contaminating protein in serum-free Mo CM was serum albumin, which accounts for the protein peak eluting at molecular weight about 68,000. Presumably, the albumin was associated with Mo cells upon transfer from serum-containing to serum-free medium. Peak fractions (24-29) were pooled, dialyzed against 0.02 M Tris, pH 7.4, containing 0.01% polyethylene glycol, and applied to a 0.9×5-cm column of DEAE-Sephadex (Pharmacia) equilibrated with the same buffer. The column was washed with several volumes of equilibration buffer and then developed with a linear NaCl gradient (from 0 to 0.4 M NaCl in equilibration buffer) with a total volume of 90 ml. Fractions of 3.6 ml were collected at a rate of 5.4 ml/hr and those with peak activity, eluting between about 0.12 and 0.20 M NaCl (total volume, 18 ml) were pooled. The pooled preparation was applied directly to a 0.9×1.0-cm column of concanavalin-A-Sepharose (Pharmacia) equilibrated with 0.02 M sodium phosphate, 0.15 M NaCl, pH 7.4, containing 0.01% polyethylene glycol. The column was washed with equilibration buffer (6 ml) and developed with equilibration buffer containing 0.2 M methyl-α-D-mannoside at the rate of about 2 ml/hr. Essentially all of the CSF activity bound to the lectin column and the bulk of the activity was eluted in the first two column volumes after the application of methyl-α-D-mannoside. Unless otherwise stated, this was the source of CSF for the biological and physical studies employing purified Mo CSF.

Polyacrylamide gel electrophoresis of the purified CSF in a native gel system (Clarke, J. T., Ann. N.Y. Acad. Sci. 121:428-436, 1964) gave multiple, poorly resolved protein bands, possibly resulting from the extensive charge heterogeneity of the CSF (see below). CSF activity was associated with several protein bands and was poorly resolved. Polyacrylamide gel electrophoresis in sodium dodecyl sulfate (Laemmli, U.K., Nature (London) 227:680-685, 1970) yielded two major protein bands, corresponding to molecular weights of about 33,000 and 18,000. CSF activity was not recovered from gel slices after extracting for 24-48 hr with buffers. Thus, it was concluded that the CSF is not homogeneous, probably constituting 40% or less of the preparation. However, the relatively high specific activity of CSF in the preparation suggests that CSF is probably not a minor protein species in the preparation.

Isoelectric Focusing

Flat-bed isoelectric focusing in granulated gel was performed using an LKB apparatus as suggested by the manufacturer. The CSF from serum-free Mo Cm was concentrated by adsorption to 1/50 volume of calcium phosphate gel (BioRad Laboratories, Richmond, CA). The CSF was eluted by incubating the gel with 2 volumes of 0.05 M sodium phosphate, pH 6.0. The eluate was dialyzed against 0.02 M Tris-HCl, pH 7.4, and incorporated into a gel slurry (100 ml total volume) containing 2.5 ml pH 4-6 ampholines, 2.5 ml pH 3.5-10 ampholines and 5 g Ultrodex-granulated gel (LKB). The mixture was dried to the proper consistency and subjected to flat-bed isoelectric focusing using 1,000 V (maximum 8 watts) for 16 hr at 5° C. The gel was subdivided and each fraction was extracted with 10 ml 0.02 M sodium phosphate, 0.15 M NaCl, pH 7.4, containing 0.01% polyethylene glycol (average moleculor weight 6,000). The fractions were dialyzed against extraction buffer and assayed.

Isoelectric focusing in polyacrylamide gel was performed as previously described (Lusis, A. J. and Pargen, K., J. Biol. Chem., 253:7336-7345, 1978) with the following modifications: Focusing was for 12 hr at 3° C. and 200 V. Gels contained 1.8% pH 4-6 ampholines (LKB) and 1.8% pH 3.5-10 ampholines. The anode reservoir contained 0.02 M sodium hydroxide and the cathode reservoir contained 0.02 M phosphoric acid.

Isolation of Mo CSF

Mo-conditioned medium

When cultured in alpha medium containing 15-20% fetal calf serum the Mo cells continuously elaborated a CSF that stimulated the formation of granulocyte-macrophage colonies in vitro. The specific activity of the conditioned medium (CM) prepared in the presence of serum was about 700 units/mg protein (using target human bone marrow cells), roughly similar to the specific activities observed using several other sources of human CSF, such as placental CM, phytohemagglutin-stimulated leukocyte CM, and lung CM. The Mo cells continued to release CSF when transferred into serum-free alpha medium, although their growth was slowed considerably. After 7 days of incubation in serum-free culture at a density of about $5 \times 10^6$ cells/ml, the medium had a specific activity in the range of 3,000 to 20,000 units/mg protein.

Purification

Because of the higher specific activity of serum-free Mo-CM, it was used as the starting material for purification experiments. A variety of fractionation methods were first surveyed using crude CM and partially purified preparations of Mo CSF. On the basis of yield and separation achieved using these methods, a purification protocol for Mo CSF was devised.

TABLE I
Purification of CSF from serum-free Mo-conditioned medium

| Fraction | Activity (units × $10^{-3}$) | Protein (mg) | Specific Activity (units mg × $10^{-3}$) | Yield (%) |
|---|---|---|---|---|
| Mo-conditioned medium | 900 | 272 | 3.3 | 100 |
| Heat treatment | 1130 | 184 | 6.1 | 125 |
| Ultrogel AcA44 | 1115 | 30 | 383 | 124 |
| DEAE-Sephadex | 381 | 0.72 | 530 | 42 |
| Concanavalin-A-Sepharose | 280 | 0.08 | 3500 | 31 |

The yield of greater than 100% during the first steps of the purification is probably due to the removal of inhibitors of colony formation present in the crude CM. The final product had a specific activity of about $3.5 \times 10^6$ units/mg protein, representing about a thousand-fold purification with an overall yield of 31%. This is the highest specific activity reported for a human CSF (using human CFU-G,M). However, as judged by electrophoresis, the CSF in this preparation was not more than about 40% pure.

Biological Activity

Dose-response curves

The responsiveness of human bone marrow cells to various concentrations of Mo CSF was determined. Curves relating the number and size of colonies observed in soft-agar cultures to the concentrations of CSF were sigmoidal. High doses of the crude conditioned medium resulted in inhibition of colony fornation; this probably results from the presence of inhibitors, since the inhibition was not observed with partially purified preparations.

Cel morpholoqy

Crude and purified Mo CSF stimulated the formation of both granulocyte and macrophage colonies. Normally, macrophage colonies predominated slightly. The ratio of colony types was not greatly dependent upon the concentration of CSF used. The fraction of macrophage colonies stimulated by Mo CSF was significantly greater than for CSFs from human PHA-stimulated leukocyte CM and human placental CM.

Species specificity

Crude Mo CM gave little or no stimulation of macrophage-granulocyte colonies using mouse bone marrow cells, while partially purified preparations of Mo CSF showed very weak stimulation. The relative stimulation of mouse, as compared to human, target cells was considerably less for Mo-CSF than for CSFs examined from other human sources.

Physical Properties

Stability

The CSF activity in crude Mo CM was stable indefinitely when stored frozen at −20° C. and for weeks when stored at 4° C. However, highly purified preparations of the CSF were relatively labile when stored either frozen or at 4° C., with the bulk of the activity being lost within days. The addition of protein (0.1% bovine serum albumin) or polyethylene glycol (0.01%) stabilized CSF preparations, and polyethylene glycol was routinely included in buffers during the latter stages of the purification of CSF. The Mo CSF was stable over a wide pH range; most of the activity was recovered after incubating the CSF in buffers between pH 3 and pH 10 at 37° C. for 1 hr or at 4° C. overnight. It was also quite stable in the presence of denaturing agents; for example, the bulk of the activity could be recovered after treating CSF for 15 hr at room temperature with either 8 M urea or 6 M guanidinc hydrochloride (in 0.02 M sodium phosphate, 0.15 M NaCl, pH 7.4).

Heat inactivation

In contrast to CSFs from placental CM and stimulated leukocyte CM, the Mo CSF was stable at temperatures up to about 70° C. Even at temperatures as high as 90° C., about half the CSF activity was recovered after 5 min of incubation. Tests were carried out in 0.02 M sodium phosphate, 0.15 M NaCl (pH 7.2), 0.1% bovine serum albumin.

Sulfhydryl reagents

Since certain CSFs are inactivated in the presence of sulfhydryl compounds, the effect of mercaptoethanol on the activity of Mo CSF was tested. In the absence of denaturing agents, exposure to concentrations of mercaptoethanol as high as 0.1 M had little effect on CSF activity. However, in the presence of 8 M urea, treatment with mercaptoethanol (1 mM) resulted in greater than 90% loss of activity.

Molecular weight

When subjected to gel exclusion chromatography, the Mo-CSF activity eluted as a single major peak, in a volume corresponding to an apparent molecular weight of about 34,000. The molecular weight of the CSF did not change during the course of purification, although the crude conditioned medium contained variable amounts of a higher molecular weight form of CSF. This latter activity had an apparent molecular weight of about 50,000 and generally comprised less than 20% of the total activity.

Isoelectric point and charge heterogeneity

Using isoelectric focusing in granulated gel, the Mo CSF from serum-free CM focused between pH 4.0 and pH 5.2. The CSF from serum-containing CM, on the other hand, was slightly more acidic, focusing between about pH 4.0 and pH 4.6. A similar charge difference was noted using ion-exchange chromatography; for example, the bulk of the activity from serum-containing medium eluted from DEAE-Sephadex (equilibrated with 0.02 M Tris, pH 7.4) between 0.18 and 0.22 M $CaCl_2$, while CSF from serum-free medium eluted over a wider range of salt concentrations, between about 0.12 and 0.22 M NaCl. In contrast to the variation in charge, the CSFs from serum-containing and serum-free Mo CM were not discernibly different in size (as judged by gel exclusion chromatography) or heat stability.

Experiments involving treatment with neuraminidase suggested that the charge heterogeneity of the CSF is due in part to the presence of varying amounts of sialic acid. When CSF preparations were subjected to isoelectric focusing in adjacent wells of polyacrylamide gels, neuraminidase treatment was found to shift the charge of the CSF toward a more basic pH. This effect was also observed using ion exchange chromatography.

Carbohydrate

The Mo CSF appears to be glycosylated, since it was bound by the lectin concanavalin-A and was eluted using methyl-α-D-mannoside. Moreover, neuraminidase treatment altered the charge, but not the activity of Mo CSF, suggesting the presence of sialic acid.

Relationship to Other Hematopoietins Present in Mo-Conditioned Medium

The Mo T-lymphocyte cells liberate into the medium several lymphokines in addition to the CSF. These include an activity that stimulates human erythroid colony formation in vitro and an activity that inhibits the migration of neutrophils. To test whether these activities resulted from distinct factors, fractions obtained after chromatographic separations of Mo CM were tested for each activity. Using gel exclusion chromatography, the CSF eluted in a volume corresponding to apparent molecular weight 34,000 and was clearly separable from the activities potentiating erythroid colony formation and inhibiting neutrophil migration, both of which eluted in a volume corresponding to molecular weight about 45,000. Moreover, the CSF was less heat stable than the latter activities. The purified CSF had little or no erythroid-potentiating activity as judged by the stimulation of human CFU-E or BFU-E in vitro; in fact, the addition of purified CSF to human erythroid cultures (BFU-E) decreased colony formation slightly.

The Mo cells elaborate and release into the medium a variety of products characteristic of activated T lymphocytes.

TABLE II
PRODUCTS OF Mo LINE

1. Colony-stimulating factor (CSF)
2. Erythroid-potentiating activity (EPA)
3. Immune interferon (type II)
4. Neutrophil migration-inhibitory factor (NIF-T)
5. T-cell growth factor (TCGF, interleukin II)
6. Macrophage-activating factor (MAF)
7. Factor stimulating fibroblast growth
8. Factor stimulating human pluripotent hematopoietic stem cell (may be same as #2)
9. Factor stimulating human leukemic cells in vitro (may be same as #1 or #2)

Among these is erythrocyte potentiating activity (EPA), which stimulates the formation of colony forming units-erythrocytes (CFU-E) and burst forming units-erythrocytes (BFU-E) colonies in cultures of human hematopoietic tissues. The purified EPA was diluted to a concentration of about 1 $\mu$g/ml using 0.02 M sodium phosphate, 0.15 M NaCl, pH 7.4 (PBS buffer), containing 0.1% bovine serum albumin (Sigma, recrystallized). Erythroid colonies were grown using a methylcellulose technique (Golde, D. W. et al., Proc. Natl. Acad. Sci. USA, 77:593-596, 1980). Cultures contained 0.5 units/ml human urinary erythropoietin (specific activity 44 units/mg protein), 0.8% methylcellulose (Dow), alpha medium (Flow), 30% fetal calf serum, 0.1 mM $\alpha$-thioglycerol, and penicillin and streptomycin. Human bone marrow CFU-E containing 8 or more hemoglobinized cells were counted after 7 days of incubation and human peripheral blood BFU-E containing 50 or more cells were counted after 14 days.

Optimum stimulation of erythroid colony formation was observed at about 20-50 $\mu$l Mo-conditioned medium (CM) per 1-ml culture dish. At higher concentrations a decrease in colony formation was observed due to the presence of inhibitory activities. The inhibition was partially removed by heat treatment and was less pronounced at low erythropoietin concentrations. Colony formation was augmented by Mo EPA at all erythropoietin concentrations tested (up to 2 units/ml).

During fractionation experiments EPA was normally assayed at a suboptimal erythropoietin concentration (0.1 unit/ml) or in the absence of added erythropoietin. In contrast to some other investigators, slight human erythroid colony formation was observed in the absence of added erythropoietin. This probably results from erythropoietin bound to target cells or present in fetal calf serum. One unit of EPA is arbitrarily defined as the amount required to stimulate human peripheral blood BFU-E by 50% in the presence of 0.5 units/ml human urinary erythropoietin.

The specific activity of EPA in serum-free Mo CM was much higher than that in serum-containing CM and, therefore, it was utilized for purification experiments. For example, after 7 days of serum-free culture at a density of $5 \times 10^6$ cells/ml, serum-free Mo CM had a specific activity of about 200 units/mg protein as compared with about 3 units/mg protein for serum-containing CM prepared under similar conditions.

The EPA in serum-free Mo CM was first partially purified and concentrated by adsorption to and elution from calcium phosphate gel. Calcium phosphate gel (36 ml) was added to 1.8 liter serum-free Mo CM containing about 0.1 mg/ml protein. After 1 hr incubation, the gel was collected by centrifugation, and the EPA was eluted by incubating the gel with two volumes of 0.05 M sodium phosphate, pH 6.0. The eluate was dialyzed against 0.02 M Tris, pH 7.4, and incorporated into a gel slurry (100 ml total volume) containing 2.5 ml pH 4-6 ampholines (LKB), 2.5 ml pH 3.5-10 ampholines, and 5 g Ultrodex ® granulated gel (LKB). The mixture was subjected to flat-bed isoelectric focusing as suggested by LKB (8 watts constant power, 5° C., 16 hr). The gel was then subdivided and fractions were extracted with PBS buffer containing 0.01% polyethylene glycol. The fractions were dialyzed against PBS buffer and assayed for EPA protein or G,M-CSF. Fractions 22-31, containing the highest specific activity of EPA, were pooled and used for further purification experiments. The eluate was then dialized and subjected to flat-bed preparative isoelectric focusing.

EPA was present primarily in acidic fractions, ranging in pH from 3.5 to 4.8. In addition, a distinct peak of activity focusing at about pH 6.5 was observed in several separate experiments. Fractions with highest EPA specific activity, ranging from about pH 3.5 to 4.6, were pooled and concentrated. The concentrate was subjected to gel exclusion chromatography using Ultrogel AcA 44. Pooled fractions of EPA from preparative isoelectric focusing were concentrated to 7 ml (using an Amicon apparatus equipped with a PM-10 membrane) and applied to a $1.6 \times 78$-cm column of Ultrogel AcA 44 (LKB) equilibrated with PBS. The column was developed with PBS at a rate of 7.2 ml/hr and fractions of 3.6 ml were collected and assayed for EPA and protein. Fractions with peak specific activity were pooled for biological and physical studies. The large peak eluting at a volume corresponding to molecular weight 68,000 probably represents serum albumin which remained associated with Mo cells upon transfer from serum-containing to serum-free medium. Peak EPA activity eluted in fractions corresponding to a molecular weight of about 40,000. Fractions with highest specific activity were pooled and used for subsequent biological and physical characterization of EPA. The final product had a specific activity of about 51,000 units/mg protein, representing about a 250-fold purification with an overall yield of about 20%. The activity measurements reflect the removal of inhibitors of erythroid colony formation present in Mo CM as well as the recovery of EPA. The purification scheme is summarized in Table III.

TABLE III

Purification of EPA from Serum-free Mo-conditioned Medium[a]

| Fraction | Activity[b] (units × $10^{-2}$) | Protein[c] (mg) | Specific Activity (units/ mg × $10^{-2}$) | Yield (%) |
|---|---|---|---|---|
| Mo-conditioned medium | 360 | 180 | 2.0 | 100 |
| Isoelectric focusing | 140 | 21 | 6.7 | 39 |
| Gel exclusion chromatography | 72 | 0.14 | 514 | 20 |

[a] Details of the purification are given in the text.
[b] Activity was determined using stimulation of human BFU-E colony formation. One unit stimulates colony formation by 50% in the presence of 0.5 unit human erythropoietin per ml.
[c] Protein was determined using a Coomasie Brilliant Blue G-250 dye binding assay.

Biological Properties

The potent inhibitors of erythroid colony formation present in the crude Mo CM were largely or completely removed by the purification procedure. The purified EPA significantly stimulated erythroid colony formation in nanogram quantities per 1-ml plat, although it was not homogeneous. Assuming a molecular weight of 45,000 for EPA, we calculate that EPA stimulates erythroid colony formation below concentrations of 0.1 nM.

The partially purified EPA stimulated both early (14-day BFU-E) and late (7-day CFU-E) human erythroid progenitors, suggesting that the two activities reside in a single factor. This possibility is supported by the observation that both activities are unusually heat stable.

Previous studies suggested that the G,M-CSF and EPA present in Mo CM are distinct since they differ in heat stability, charge and molecular weight. Our present findings support this conclusion since the partially purified EPA contained little or no CSF activity. Moreover, a highly purified preparation of Mo CSF was found to inhibit, rather than stimulate, erythroid colony formation.

The partially purified EPA preparation retained an activity stimulating mixed erythroid-granulocyte-megakaryocyte colony formation in vitro. In addition, the activity stimulating mixed colonies was, like EPA, exceptionally heat stable. This raises the possibility that the activities stimulating BFU-E and the multipotent myeloid stem cell detected in vitro result from the same factor. Alternatively, the two activities may reside in separate but structurally similar factors, possibly members of a family of closely related, homologous proteins. The sources of activities stimulating formation of mixed myeloid colonies in vitro all contain activities stimulating committed erythroid progenitors as well.

Partially purified EPA, but not crude Mo CM, stimulates the clonal growth of mouse Friend erythroleukemia cells and of human K562 leukemia cells. Certain sublines of K562, including the one tested, exhibit properties characteristic of erythroleukemia cells.

The following is a summary of observed EPA properties. EPA appears to be glycoprotein in nature, since it binds to concanavalin A-Sepharose and is destroyed by treatment with proteases. It exhibits remarkable heat stability and is highly resistant to denaturing agents. When subjected to gel exclusion chromatography at neutral pH the bulk of the activity eluted in a peak of apparent molecular weight about 45,000, although a higher molecular weight shoulder was also observed. This shoulder was diminished after partial purification. Using isoelectric focusing, a broad major peak of EPA was observed in the acid regions of the gradient; in addition, a second peak of activity focusing at about neutral pH was observed in four separate experiments. The origin of the size and charge heterogeneity is not clear. In view of the complexity of the clonal assay procedure, the presence of multiple modulator activities in Mo CM would not be surprising. Also, EPA could exhibit heterogeneity in the degree of modification (e.g., glycosylation or proteolytic cleavage) or form complexes with other constituents in the medium.

The neutrophil migration inhibition factor was isolated and characterized as follows.

Lymphocyte Culture Techniques

Mononuclear cells were isolated from heparinized human peripheral blood by Ficoll-Hypaque gradient centrifugation and washed with Hanks' buffered salt solution (BSS). Mononuclear cells were cultured at $3 \times 10^6$/ml for 24 hr at 37° C. in the presence of 5% $CO_2$ in Medium 199 (Flow Laboratories, Anaheim, Calif.) with 20 mM Hepes buffer, penicillin, 100 units/ml, and streptomycin, 100 μg/ml. Stimulated cultures contained concanavalin A (Con A), 25 μg/ml. After 24 hr, the cell-free supernatants were harvested, and the nonstimulated culture supernatants were reconstituted with the same concentration of Con A. All cultures were viable as determined by trypan blue exclusion. The T-lymphoblast cell lines 8402 (established from a patient with acute lymphoblastic leukemia) and Mo were cultured similarly, except that Con A was not used. Mo cells spontaneously produce a migration inhibition factor for neutrophils whereas other lymphoblast cell lines including 8402 do not. Moreover, 8402 could not be stimulated to produce such an activity in the presence of mitogen. Therefore, the 8402 cells were used as a control for Mo cells in these studies. All culture supernatants were stored at -20° C. until assayed.

Microassay for Neutrophil Migration

The details of this assay have been reported (Weisbart, R. H. and Mickey, M. R., J. Immunol. Methods 16:269, 1972). Briefly, neutrophils were purified (97-99%) from the peripheral blood of healthy subjects by Ficol-Hypaque gradient centrifugation, and the red blood cells were removed by dextran sedimentation. Four microliters of a neutrophil suspension ($50 \times 10^6$/ml) were mixed with 4 μl of cell culture supernatants and incubated for 30 min at 37° C. One-microliter aliquots of these neutrophil-supernatant suspensions were then distributed into quadruplicate 1.5-mm diameter wells cut in a 1% agarose gel that contained Medium 199 with 10 mM Hepes buffer and 10% horse serum. The wells were filled under mineral oil in 150-mm round culture dishes (Integrid, Falcon Plastics, Oxnard, Calif.) with 128 migrations on each dish. After the neutrophils migrated overnight, the cells were fixed with ethyl alcohol and the agarose gel was removed. The largest diameter of each migration was measured with an ocular micrometer, and the data were expressed as the percentage inhibition in the area of migration.

Heat Stability of Neutrophil Migration Inhibition Activity

Control and active serum-free culture supernatants were heated at 60°, 80°, and 100° C. for 10 to 30 min and centrifuged at 2000 g for 10 min. The supernatant fractions were decanted and assayed for neutrophil migration inhibition activity.

Effect of Pronase on Neutrophil Migration Inhibition Activity

Pronase was added to 0.5-ml aliquots of control and active culture supernatants (1 mg/ml final concentration) and incubated at 37° C. for 30 min. The supernatants were then heated to 80° C. for 15 min to inactivate the pronase. The supernatants were assayed for neutrophil migration inhibition activity.

Affinity of Con A Sepharose for Neutrophil Migration Inhibition Activity

Sepharose beads coated with Con A (Pharmacia, Piscataway, N.J.) were washed with Hanks' BSS, and 0.1 ml of packed beads were incubated at 37° C. for 30 min with 0.5 ml of control (8402) and active (Mo) lymphoblast culture supernatants with constant mixing. In addition, PBL were cultured with sepharose beads alone, and with Con A sepharose for 24 hr. The beads were recovered by centrifugation, washed with Hanks' BSS, and eluted at 24° C. for 30 min with 0.5 ml of 10% α-methyl-D-glucoside in 0.1 M acetate buffer, pH 6.0, containing 1 M NaCl, $10^{-3}$ M $CaCl_2$, $10^{-3}$ M $MgCl_2$, and $10^{-3}$ M $MnCl_2$. The eluates were dialyzed against Hanks' BSS. Aliquots of original supernatants and the dialyzed eluates were assayed for neutrophil migration inhibition activity.

Isolation of Neutrophil Migration Inhibition Activity by Electrophoresis in Polyacrylamide Gradient Slab Gels Neutrophil migration inhibition activity was concentrated from culture supernatants by treatment with diethylaminoethyl (DEAE) Sephacel (Pharmacia, Piscataway, N.J.). Batch method preparation was used with sterilized beads and buffers. Ten milliliters of PBL or lymphoblast culture supernatants was dialyzed against 0.1 M trischloride, pH 8.0, and incubated at 24° C. for 30 min with 2 ml of packed beads. The beads were eluted in 1 ml of 0.3 M NaCl. The eluates were dialyzed against distilled water, lyophilized, and reconstituted with 20 μl of Hanks' BSS. In preliminary experiments substantial migration inhibition activity was demonstrated in these preparations. Fivemicroliter aliquots of DEAE Sephacel purified and concentrated material were applied to preformed polyacrylamide gradient slab gels (PAA 4/30 Pharmacia, Piscataway, N.J.) and electrophoresed for 4 hr at 300 V in 1% trisborate buffer, pH 8.1. Control and test supernatants were electrophoresed simultaneously on the same gel, and corresponding fractions of each were compared for biological activity. Hen egg albumin (45,000 daltons) and bovine serum albumin (67,000 daltons) markers were electrophoresed on the opposite half of the gel. Horse serum was electrophoresed to provide column markers. Purified hemoglobin A (Gelman, Ann Arbor, Mich.) was electrophoresed on both halves of the slab gel. The gel was sectioned and the half of the gel containing the standards was stained with amido black and destained by electrophoresis. The two halves of the gel were then aligned by superimposition of the hemoglobin bands. Portions of the gel containing the control and test samples were sectioned and eluted by electrophoresis (140 V for 16 hr) into 50-μl dialysis chambers formed in Lucite. The eluates were dialyzed against Hanks' BSS and tested for neutrophil migration inhibition activity.

Treatment of Culture Supernatants with Diisopropyl Fluorophosphate (DFP)

The culture supernatants (Mo T, pH 8.9, and peripheral blood lymphocytes, pH 7.2) were treated with DFP to provide final concentrations of $10^{-3}$, $10^{-4}$, and $10^{-5}$ M DFP. Ten microliters of the appropriate dilution of a 5% stock solution of DFP in isopropyl alcohol was incubated with 0.5 ml of the control and active culture supernatants for 30 min at 37° C. DFP-Treated supernatants were assayed before and after dialysis against Hanks' BSS.

In order to test the efficacy of this procedure in destroying serine esterase activity thought to be present in the culture supernatants, 0.25 ml samples of both active supernatant (Mo T and PBL) were incubated as described above following addition of 2.5 μg bovine trypsin in 25 μl of 1.2 $10^{-3}$ M Tris HCl containing $5 \times 10^{-5}$ M $CaCl_2$. Two control samples containing trypsin but no DFP were incubated similarly. Trypsin activity in all samples was determined at the start and end of the experiment by incubating a 10-μl aliquot with a mixture of 0.49 ml of 0.1 M Tris HCl, pH 8.2, containing $2.5 \times 10^{-3}$ M $CaCl_2$, Triton X-100 (1:4000, and 0.4 ml of an aqueous solution of carbobenzoxyglycylglycylarginyl-2-naphthylamide (90 mg/100 ml) in a water bath at 25° C. for 15 min. The reaction was terminated by addition of 0.1 ml 1 M citrate buffer, pH 4.5, and fluorescence measured at $\lambda_{EX}$ 345 nm, $\lambda_{EM}$ 415 nm (uncorrected) (Penderknecht, H. et al., Clin. Chim. Acta 73:369, 1976).

Reversibility of Neutrophil Migration Inhibition Activity

Supernatants from control and Con A stimulated peripheral blood lymphocyte cultures and the lymphoblast cells 8402 and Mo were preincubated for 30 min at 37° C. with purified human neutrophils. The cells were then washed with Hanks' BSS, resuspended in Medium 199 with 10% horse serum, and incubated at 24° C. Aliquots of the neutrophils were removed at 2, 4, and 20 hr, washed with Hanks' BSS, and the cell concentration was adjusted to $25 \times 10^6$/ml viable cells. One-microliter aliquots of cells were dispensed in agarose wells and the migrations were assessed as previously described.

Heat Stability of Neutrophil Migration Inhibition Activity

The results of heating serum-free supernatants containing neutrophil migration inhibition activity from peripheral blood lymphocytes and the T-lymphoblast cell line, Mo, are shown in Table IV.

TABLE IV

| | Heat Stability of Neutrophil Migration Inhibition Activity | | | |
|---|---|---|---|---|
| | Time | Initial | Temperature (°C.) | | |
| Source | (min) | activity | 60 | 80 | 100 |
| Mo cells | | 38 ± 4 | | | |

TABLE IV-continued
Heat Stability of Neutrophil Migration Inhibition Activity

| Source | Time (min) | Initial activity | Temperature (°C.) 60 | 80 | 100 |
|---|---|---|---|---|---|
|  | 5 |  | — | — | 43 ± 6[a] |
|  | 10 |  | 34 ± 3 | 34 ± 6 | 15 ± 6 |
|  | 30 |  | 32 ± 5 | 28 ± 6 | 4 ± 6 |
| PBL |  | 50 ± 4 |  |  |  |
|  | 5 |  | — | — | 49 ± 3 |
|  | 10 |  | 45 ± 5 | 30 ± 6 | 13 ± 5 |
|  | 30 |  | 48 ± 3 | 34 ± 4 | −4 ± 4 |

[a]Percentage inhibition in the area of neutrophil migration ± SEM.

Similar heat stabilities were demonstrated for the inhibition activities from PBL and Mo cells, with full stability at 60° and 80° C. for 30 min. Neutrophil migration inhibition activity was stable even after boiling for 5 min. The activity was destroyed, however, after boiling for longer periods of time.

Effect of Pronase on Neutrophil Migration Inhibition Activity

Before treatment with pronase, serum-free supernatants from Mo cells and Con A induced PBL showed 56±6% and 42±4% inhibition in the area of neutrophil migration, respectively, compared to supernatants from 8402 cells and nonstimulated PBL. After treatment with pronase, the Mo and PBL activities were abolished (−4±6% and 4±4% inhibition in the area of migration). Control supernatants containing pronase that were heated to 80° C. for 15 min did not inhibit neutrophil migration in comparison to supernatants that did not contain pronase. Supernatants heated to 80° C. did not lose migration inhibition activity as shown above.

Affinity of Con A Sepharose for Neutrophil Migration Inhibition Activity

All of the neutrophil migration inhibition activity in supernatants from Mo cells was removed by Con A Sepharose with 37±4% inhibition in the area of migration before and 0±11% after incubation with Con A Sepharose. Full activity was recovered after elution with α-methyl-D-glucoside (45±7% inhibition). The dialyzed eluates of Con A Sepharose cultured with PBL gave 41±5% inhibition in the area of migration of neutrophils compared to the eluates of Sepharose beads without Con A similarly cultured with PBL.

Isolation of Neutrophil Migration Inhibition Activity by Electrophoresis in Polyacrylamide Gradient Slab Gels The biological activities identified in eluates of the various fractions are shown in Table V.

TABLE V
Isolation of Neutrophil Migration Inhibition Activity By Polyacrylamide Gel Electrophoresis

| Gel fractions | Distance[a] (mm) | Markers (daltons) | Source PBL | Mo cells |
|---|---|---|---|---|
| 6 | 54 |  | 9 ± 6[b] | 15 ± 5 |
| 5 | 5 |  | 4 ± 10 | −6 ± 6 |
| 4 | 5 | 67,000(BSA) | 4 ± 6 | 0 ± 6 |
| 3 | 5 |  | 4 ± 9 | 5 ± 10 |
| 2 | 5 | 45,000(HEA) | 0 ± 8 | 28 ± 5 |
| 1 | 5 |  | 26 ± 5 | 37 ± 7 |

[a]Distance from the bottom (low MW end) of the gel.
[b]Percentage inhibition in the area of neutrophil migration ± SEM Migration inhibition activity from PBL was localized to the pre 45,000 dalton-region with no substantial activity identified elsewhere on the gel. Activity was obtained from the Mo supernatants in the 45,000-dalton region as well as the region corresponding to 35,000 to 45,000 daltons.

Effect of Treatment of Culture Supernatants with Diisopropyl Fluorophosphate DFP)

The effect of DFP on neutrophil migration inhibition activity from supernatants of PBL, Mo cells, and a partially purified preparation from Mo isolated by polyacrylamide gel electrophoresis were determined. There was no effect on the migration inhibition activity at $10^{-3}$, $10^{-4}$, or $10^{-5}$ M DFP. The efficacy of DFP in destroying serine esterase activity was demonstrated by adding trypsin to an aliquot of the supernatants tested, and assaying for the presence of trypsin in the presence and absence of DFP. In the samples containing trypsin and DFP ($10^{-3}$ M), more than 99% of trypsin activity was destroyed; in the samples containing trypsin but no DFP, only 4% of trypsin activity was lost. These results demonstrate the complete removal of serine esterase by the above treatment with DFP.

Reversibility of Neutrophil Migration Inhibition Activity

Neutrophils that were incubated with activated supernatants, washed, and cultured for 2 hr, showed maximum inhibition of migration. If the neutrophils exposed to activated supernatants were washed and left at 24° C. for 20 hr, rewashed, and migrated, the inhibition activity was lost. Neutrophils treated in this way could still be inhibited by activated supernatants. When reincubated with active supernatants for 30 min and migrated, the neutrophils were inhibited in their migration 39±6%. Neutrophils were viable at 24 hr as evidenced by their ability to migrate and respond to activated supernatants.

The immune interferon is produced as follows in a conditioned medium. Single cell suspensions in minimum essential medium supplemented with non-essential amino acids (F-15) and 10% FCS are seeded into 16 mm wells at a density such that at 37° C., confluence is achieved in about 20 hrs. post-plating. After achieving confluence, the medium is removed, the cell cultures washed twice, and phorbol esters in about 1-100 μg/ml with phytohemeagglutinin in about 1-100 μg/ml are added. After 15 hrs. at 37° C., the cells are separated from the supernatant, and the interferon activity of the medium determined. Human virus susceptible cells of single cell suspension in appropriate nutrient medium are seeded into 16 mm wells at a density such that at 37°, confluence is achieved within about 20 hrs. post-plating. After achieving confluence, the medium is removed, the cultures washed twice, and an appropriate virus at an input multiplicity of infection (MOI) equal to 7 added in a nutrient medium containing varying amounts of the Mo conditioned medium. The virus is absorbed at 37° C. for 30 mins. At the end of this period and again 90 min. post infection, the monolayers are washed twice and one ml of fresh nutrient medium added. After 15 hrs. at 37° C., the cultures are harvested and the yield of the virus determined. In accordance with the above test, the Type 2 immune interferon produced by the Mo cell line is effective in reducing the amount of virus produced, as compared to control samples where no Mo conditioned medium is present.

In addition to obtaining the individual factors by cultivation of the Mo cell line, isolation of the conditioned medium, and separation and purification of the desired protein factor, the individual factors can be produced by hybrid DNA technology.

The Mo cells are homogenized and cytoplasmic RNA purified from a postnuclear supernatant by $Mg^{2+}$ precipitation. (Palmiter, R. (1974) Biochemistry 13, 3603-3615). The precipitate is extracted with phenol and chloroform and enriched for poly(A)-containing RNA by oligo (dT)-cellulose chromatography. (Avir, H. and Leder, P., (1972) Proc. Nat. Acad. Sci. USA 69, 1408-1412.

The RNA is washed with 0.01 M Tris HCl (pH 7.5)-0.5 M KCl with 100$A_{260}$ units of RNA dissolved in the above buffer applied to a 2 ml column previously washed with buffer. After eluting non-absorbed material, the absorbed material was eluted by washing initially with 0.01 M Tris-HCl (pH 7.5)-0.1 M KCl, followed by 0.01 M Tris-HCl (pH 7.5). The eluted material was precipitated in 2% potassum acetate (pH 5.5) with two volumes of ethanol, and the mixture allowed to stand overnight at $-20°$ C. The precipitate was dissolved in a solution containing 10 mM Tris-HCl/1 mM EDTA (pH 7.4) and disaggregated by heating at 80° for 1 hr.

The desired mRNA is isolated as follows, as described in Alwine et al., Proc. Nat. Acad. Sci USA (1977) 12, 5350-5354. See also U.S. Pat. No. 4,139,346 and Reiser et al. Biochem. Biophys. Res. Comm., 85, 1104 (1978).

The mRNA is separated by electrophoresis on a horizontal slab gel ($23 \times 14 \times 0.4$ cm) containing 1.5% agarose and 4 mM methyl mercuric hydroxide. Samples in water are mixed with an equal volume of starting buffer [$1 \times E$ buffer/10% glycerol/bromphenol blue] (for E buffer, see Bailey and Davidson (1976) Anal. Biochem. 70, 75-85) and made 10 mM in methyl mercuric hydroxide.

DBM paper is prepared as described in Alwine et al., supra. After electrophoresis, a strip of DBM paper saturated with 50 mM sodium borate buffer (pH 8.0) is placed on the gel with Plexiglas strips positioned to prevent the DBM-paper from contacting the two layers of Whatman 3 MM paper saturated with the borate buffer underlying the gel. The DBM-paper is then repetitively covered with two layers of dry 3 MM paper, several layers of paper towels and a Plexiglas weight and the buffer allowed to soak through before each change.

The position of the desired mRNA is determined using a probe prepared as follows. From the amino acid sequence of the desired factor a DNA sequence is synthesized as described in European Patent No. 0001931. The DNA sequence will be from about thirty to sixty bases. By employing derivatized bases, codons are prepared which are then coupled with other codons to produce oligodeoxyribonucleotides of from 9 to 18 bases. The oligodeoxynucleotides are then combined to prepare the DNA probe. The probe is then labeled with $^{32}P$ employing [$\alpha$-$^{32}P$]-ATP and polynucleotide kinase.

Hybridization of the RNA with the DNA probes is performed in accordance with the method of Denhardt (1966) Biochem. Biophys. Res. Comm. 23, 641-652. The paper strips containing transferred RNA are treated for at least four hours at 42° C. with hybridization buffer (50% formamide/0.75 M NaCl/75 mM sodium citrate containing 0.02% wt/vol each of bovine serum albumin, ficoll and polyvinylpyrrolidone, 1.0-2.5 mg of sonicated denatured calf thymus DNA/ml and 1% wt/vol glycine. Hybridizations are performed by placing the paper strips, hybridization buffer without glycine (50-100 $\mu$l/cm$^2$ of paper surface area), and the single-stranded $^{32}P$ labeled probe ($\sim 5 \times 10^4$ cpm/cm$^2$ of paper surface area; $\sim 5 \times 10^7$ cpm/$\mu$g) into plastic boiling bags from which the excess air is removed prior to sealing by heat. After laying the bags horizontally and gently rocking for 36 hr. at 42° C., the paper is washed at 42° C. for at least 4 hrs. with at least 6 changes of a 50% formamide/0.75 M NaCl/75 mM sodium citrate solution. After blotting to remove excess solution, the paper strips are covered with Saran ® wrap and visualized autoradiographically with Kodak XF-5 X-ray film. The band to which the probe hybridized is excised from the electrophoretic gel to provide the desired mRNA.

The mRNA is used to make cDNA as follows. The reaction is carried out in 100 $\mu$l using approximately 5 $\mu$g mRNA, 45 units avian myeloblastosis virus reverse transcriptase and dCTP labeled to 4 Ci/mmole. In $\sim 30$ min, $\sim 1.5$ $\mu$g cDNA is synthesized. The reaction is terminated by adding EDTA (to 10 mM), followed by extraction with phenol, then ether and then passing the mixture over a Sephadex G-50 fine column in 10 mM Tris (pH 7.4), 2 mM EDTA, 10 mM NaCl (TEN). The void volume is collected, precipitated with ethanol, centrifuged and the RNA hydrolyzed with NaOH. The cDNA is isolated and used as a template for dsDNA.

The formation of dsDNA is achieved by combining in 100 $\mu$l 1.1 $\mu$g cDNA, 10 units DNA polymerase I and 200 $\mu$M of each deoxynucleotide triphosphate with dCTP adjusted to 30 Ci/mmole and the reaction allowed to proceed for 10 min. at 42° C. The reaction is stopped and and extracted as above before being passed over a Sephadex G-50 fine column in TEN containing only 0.1 mM EDTA. Column fractions containing the ds cDNA were pooled avoiding the inclusion of unincorporated deoxynucleoside triphosphates and the mixture adjusted to 30 mM sodium acetate (pH 4.5), 3 mM $ZnCl_2$, 10 $\mu$g of native and 10 $\mu$g denatured salmon sperm DNA/ml.

Purified A. oryzae single strand specific nuclease S1 is added to a final concentration of 5 units/ml (1 unit- =amount required to completely degrade 10 $\mu$g denatured DNA in the presence of 10 $\mu$g native DNA in a 2 hr. incubation at 37° in above described S1 buffer). After 1 hr. at 37° C. the digestion is stopped by ice-cooling and adding SDS to a final concentration of 1%. After adding about 10 $\mu$g of E. coli tRNA, the mixture is extracted at r.t. with an equal volume of chloroform and the organic phase re-extracted with S1 buffer. After precipitation by the addition of 2.5 volumes ethanol at $-20°$ C. overnight, terminal addition of dCTP to the ds cDNA by terminal deoxynucleotidyl transferase was performed with 1 $\mu$g ds cDNA in 500 $\mu$l containing 140 mM cacodylic acid, 30 mM Tris base, 110 mM KOH (final pH 7.6), 0.1 mM dithiothreitol, sufficient dCTP to provide about $10^3$ pM 3' termini/$\mu$l and 0.5 $\mu$l ($2.3 \times 10^5$ units/ml) of the transferase. After sufficient time to add about 30 dC residues per 3' terminus ($\sim 10$ min) at 37° C., the reaction is cooled, extracted, desalted and precipitated as described above. The dC-tailed ds cDNA is then preparatively electrophoresed on a 1.7% agarose gel in Tris-acetate-NaCl (Dugarczyk et al. J. Mol. Biol. 96, 171-184 (1975)), cut out of the gel and electrophoretically eluted into a dialysis bag (McDonnell et al. J. Mol. Biol. 110, 119-146 (1977). After centrifugation, the dC-tailed ds cDNA is redissolved in 10 mM Tris-HCl (pH 7.4), 0.25 mM EDTA, 100 mM NaCl.

The ds cDNA is inserted into the PstI site of plasmid pBR322 by linearizing pBR322 DNA with PstI and adding approximately 15 dG residues per 3' end by the procedure described for dC-tailing, substituting dGTP for dCTP (See also, Roychoudbury et al. Nucleic Acids Res. 3, 101–116 (1976)). After extraction with phenol and ethanol precipitation the dG-tailed pBR322 is combined with the dC-tailed ds cDNA at a weight ratio of about 1:1 in 10 mM Tris (pH 8) and dialyzed against 0.1 M NaCl, 10 mM EDTA, 10 mM Tris (pH 8). After heating the mixture (4 ml) at 56° C. for 2 min, the mixture is heated at 42° C. for 2 hrs.

The resulting plasmids are introduced into $\chi^{1776}$ using a modification of the transfection procedure described by Errea et al. J. Mol. Biol. 96, 495–509 (1975). Into 100 ml of L broth supplemented with diaminopimelic acid (DAP 50 μg/ml) and thymidine (4 μg/ml), is inoculated 1 ml of an overnight bacterial culture and the bacterial culture grown until exponential phase at 35° C. and then harvested by centrifugation at 4° C. After washing the cells in 0.3 volume 10 mM NaCl, the cells are resuspended in 30 ml freshly prepared MCN buffer (70 mM MnCl$_2$, 40 mM NaOAc (pH 5.6) and 30 mM CaCl$_2$) and chilled on ice for 20 min. Cells are collected, resuspended in 1 ml MCN buffer and added in 200 μl aliquots to 50 μl DNA in TEN buffer (10 mM Tris-HCl (pH 7.5), 0.1 mM EDTA, 50 mM NaCl). After chilling for 30 min. at 0° C., the mixtures are incubated at 27° C. for 5 min., chilled again for 30 min. and 50 μl aliquots plated onto Penassaybroth agar supplemented with DAP and thymidine. Plates containing transformants are incubated at 32° C. and colonies scored 2 to 3 days after plating.

Colonies are screened by the HART method (Patersen et al. Proc. Natl. Acad. Sci. USA 74, 4370–4374 (1977)) by digesting plasmid DNA isolated from the clones with PstI, precipitating with ethanol and dissolving directly into 20 μl deionized formamide. After heating for 1 min. at 95° C., each sample is placed on ice. The samples are mixed with 1.5 μg oligo dT-cellulose bound RNA, 10 mM PIPES (pH 6.4), 0.4 M NaCl and incubated for 2 hr. at 50° C. After diluting with 75 μl H$_2$O and ethanol and adding 10 μg wheat-germ tRNA, the precipitate is washed with 70% ethanol, dissolved in H$_2$O, and added to a wheat-germ cell-free translation mixture (Roberts et al. Proc. Natl. Acad. Sci. USA 70, 2330–2334 (1973)). After 3 hrs. at 23° C., the reaction mixture is treated with ribonuclease and analyzed for the presence of the desired protein by an immunoassay, if antibodies are available, or by a bioassay after purification by conventional techniques described previously.

The clone(s) shown to produce the desired protein may then be expanded and used for the production of the desired protein product.

It is evident from the above results, that a conditioned medium can be produced by cultivating Mo cells which can be used for a wide variety of growth and regulatory factors, such as erythroipoietic and colony stimulating factor, immune interferon, neturophil migration-inhibition factor, as well as others previously indicated. The conditioned medium can be used for directing cell differentiation to the growth of a particular type of cell, for protection of cells in vitro from destruction by viral invasion, and for the production of various proteins which may be isolated from the conditioned medium. In addition, the cells provide a source for messenger RNA as well as chromosomal DNA which can be used in hybrid DNA technology for the formation of plasmids for transformation of microorganisms. The resulting transformed microorganisms can then be used for the production of the individual factors.

Although the foregoing invention has been described in some detail by way of illustration and example for purposes of clarity of understanding, it will be obvious that certain changes and modifications may be practiced within the scope of the appended claims.

What is claimed is:

1. A method for producing in isolatable amounts an excretory protein produced by a T-lymphocyte, said method comprising:
   cultivating as a single cell suspension the Mo cell line in a nutrient medium, whereby said excretory proteins are produced and excreted into said nutrient medium.

2. A method according to claim 1, wherein at least one of said proteins is a member of the group consisting of colony stimulating factor, erythroid potentiating factor, neutrophil migration inhibition factor and immune interferon Type II.

3. A method according to claim 2, wherein said protein is immune interferon, Type II.

4. A method according to claim 2, wherein said protein is colony stimulating factor.

5. A method according to claim 2, wherein said protein is erythroid potentiating factor 6. A method according to claim 2, wherein said protein is neutrophil migration inhibition factor.

7. A method according to claims 3, 4, 5, or 6, including the step of isolating and purifying said protein.

8. A method for cloning DNA including a gene capable of expressing a protein product produced by a T-lymphocyte, said method comprising:
   isolating messenger RNA from Mo cells;
   separating the messenger RNA coding for expression for a predetermined polypeptide from other messenger RNA;
   generating cDNA with reverse transcriptase from said messenger RNA;
   preparing double-stranded DNA from said cDNA employing DNA polymerase;
   inserting said double-stranded DNA into a vector; and
   transforming a host with said vector, whereby said double-stranded DNA is cloned.

9. A method according to claim 8, wherein said double stranded DNA is inserted into said vector to provide expression of said double-stranded DNA; and including the additional step of isolating protein expressed by said double-stranded DNA.

10. A method according to claim 9, wherein said protein is immune interferon, Type II.

11. A method according to claim 9, wherein said protein is erythroid potentiating factor.

12. A method according to claim 9, wherein said protein is colony stimulating factor.

13. A method according to claim 10, wherein said protein is neutrophil migration inhibition factor.

14. A protein composition comprising erythroid potentiating factor in an amount of at least about 50,000 units/mg.

15. A protein composition comprising colony stimulating factor in an amount sufficient to provide at least about 10 units/mg.

16. A single cell suspension of the Mo cell line in a nutrient medium.

17. A single cell suspension according to claim 16, wherein said nutrient medium is serum free.

18. A single cell suspension according to claim 16, wherein said nutrient medium contains serum.

19. A genetic library comprising DNA fragments derived by restriction cleavage of DNA from the Mo cell line.

20. A method for stimulating the poliferation of human bone marrow cells, which comprises contacting said bone marrow cells an amount sufficient to cause proliferation of a composition according to claim 4.

21. A method for stimulating the proliferation of erythrocytes which comprises contacting human bone marrow cells in the presence of erythropoietin with a composition according to claim 5 in an amount sufficient to cause proliferation.

22. A method for inhibiting viral lysis of a human cell susceptible to viral lysis which comprises applying an inhibiting amount to a host human cell of a composition according to claim 3.

* * * * *

UNITED STATES PATENT AND TRADEMARK OFFICE
CERTIFICATE OF CORRECTION

PATENT NO. : 4,438,032
DATED : March 20, 1984
INVENTOR(S) : David W. Golde et al.

It is certified that error appears in the above—identified patent and that said Letters Patent is hereby corrected as shown below:

On the title page of the patent add as a second paragraph to the ABSTRACT:

--The Mo line has been deposited at the A.T.C.C. on June 3, 1981, with the Accession No. CRL 8066.--

Signed and Sealed this

Nineteenth Day of March 1985

[SEAL]

Attest:

DONALD J. QUIGG

Attesting Officer

Acting Commissioner of Patents and Trademarks